United States Patent [19]

Piet et al.

[11] 4,059,903
[45] Nov. 29, 1977

[54] CONTROLLED ENVIRONMENT WORK ENCLOSURE

[75] Inventors: Meyer Piet, Arcadia; Dean Gaylord Giles, Valinda, both of Calif.

[73] Assignee: Futurecraft Corporation, City of Industry, Calif.

[21] Appl. No.: 672,510

[22] Filed: Mar. 31, 1976

[51] Int. Cl.² .............................................. A61C 3/00
[52] U.S. Cl. ..................................... 32/40 R; 23/259
[58] Field of Search .................. 128/1 R, 1 B; 312/1; 98/115 R, 115 LH; 55/DIG. 18; 23/259, 252

[56] References Cited

U.S. PATENT DOCUMENTS

| 3,070,086 | 12/1962 | Smith et al. | 128/1 B |
| 3,335,713 | 8/1967 | Grosholz et al. | 128/1 B |
| 3,907,389 | 9/1975 | Cox et al. | 128/1 B |

Primary Examiner—Robert Peshock
Attorney, Agent, or Firm—James E. Brunton

[57] ABSTRACT

A controlled atmosphere work enclosure for use in handling hazardous materials such as mercury and mercury alloys. The work enclosure comprises a hollow housing defining a workspace having disposed intermediate thereof a perforated work platform upon which an amalgamator unit or the like can be mounted. Replaceable flexible plastic or rubber gloves are sealably affixed to glove rings mounted on the front of the unit to permit convenient working access to the platform. Filtered air inlets are provided above the work platform and a filtered air outlet is installed below the platform. Fan units are provided proximate the floor to maintain subatmospheric pressure within the enclosure and to cause air to be continuously drawn inwardly through the air inlets, rapidly downward past and through the work platform and outwardly through the filtered outlet. Use of the enclosure permits hazardous materials to be safely and expeditiously handled and stored without fear of environmental contamination.

10 Claims, 4 Drawing Figures

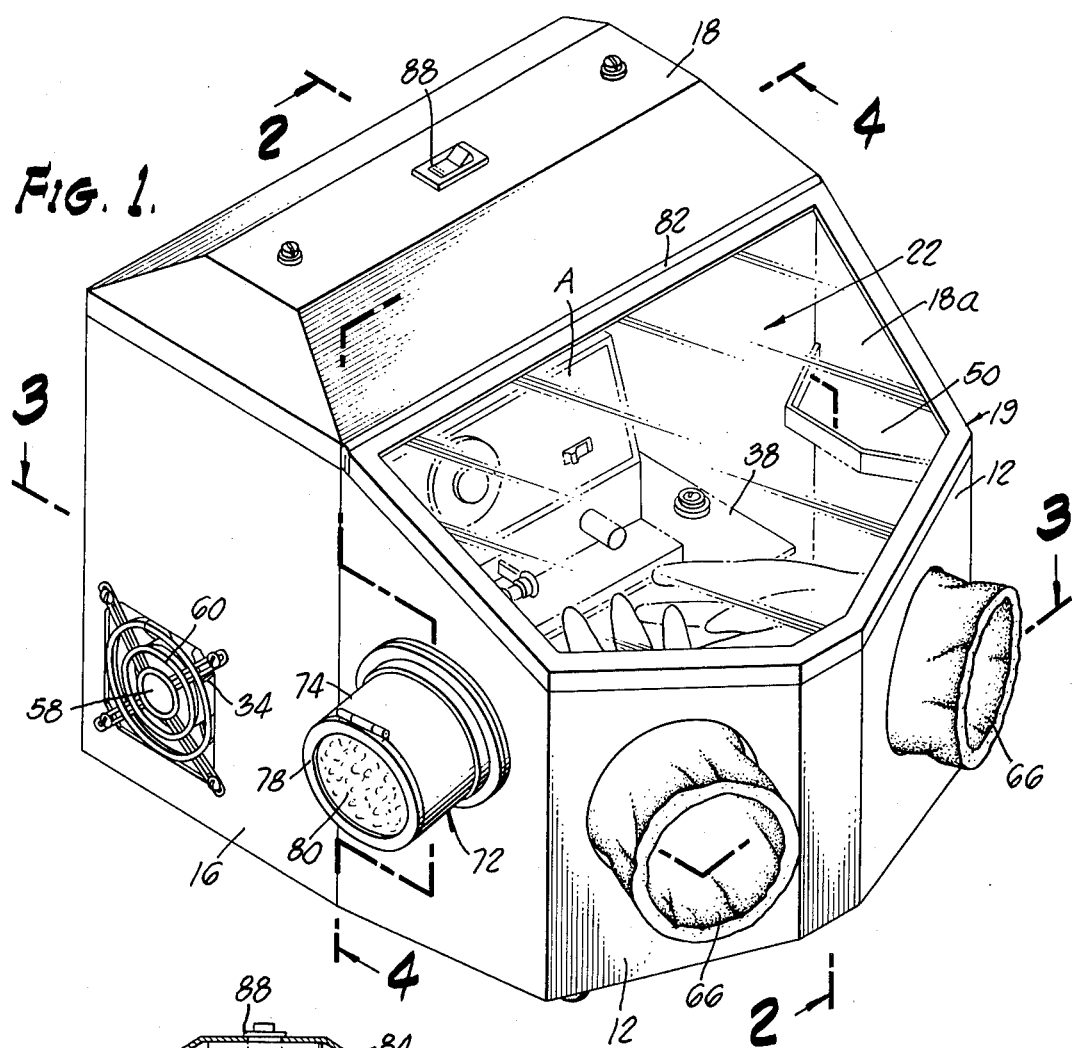
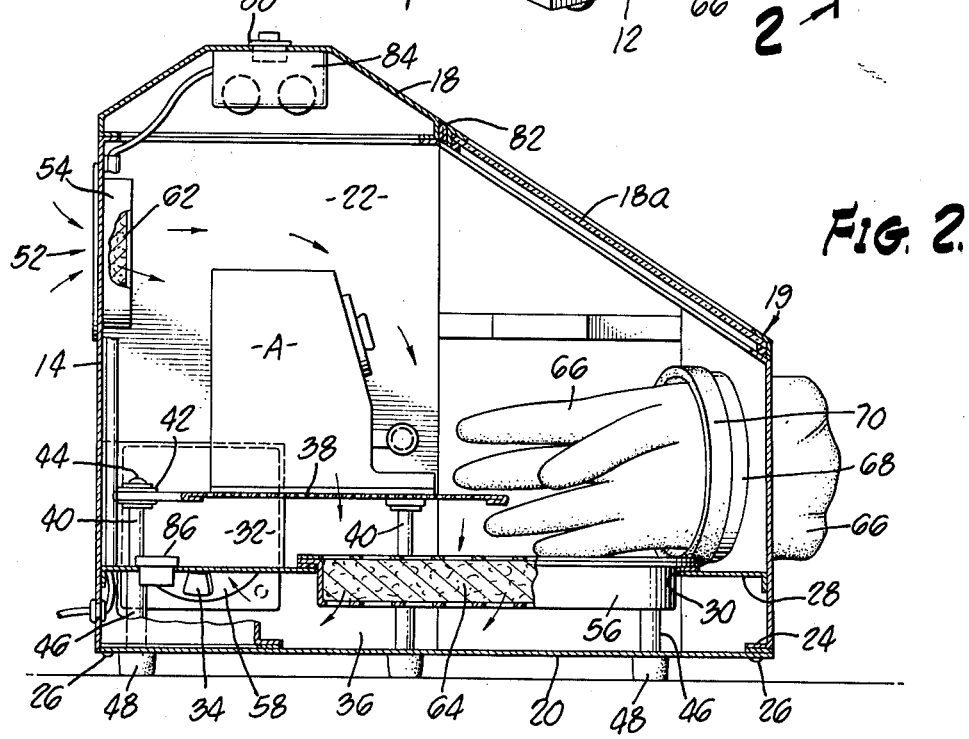

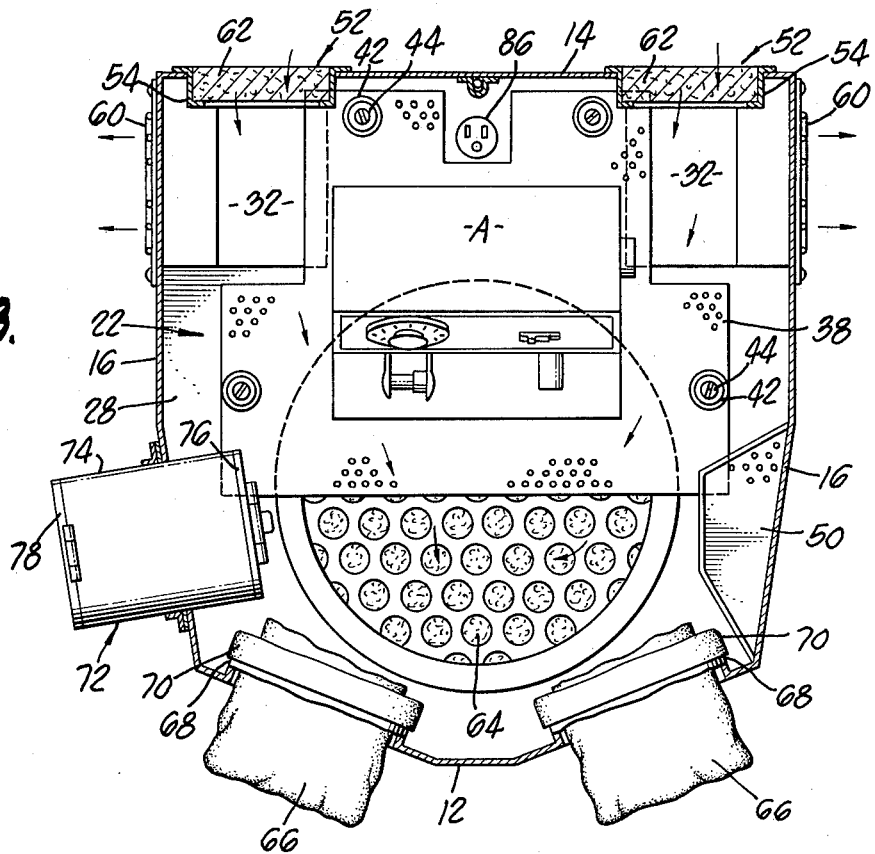
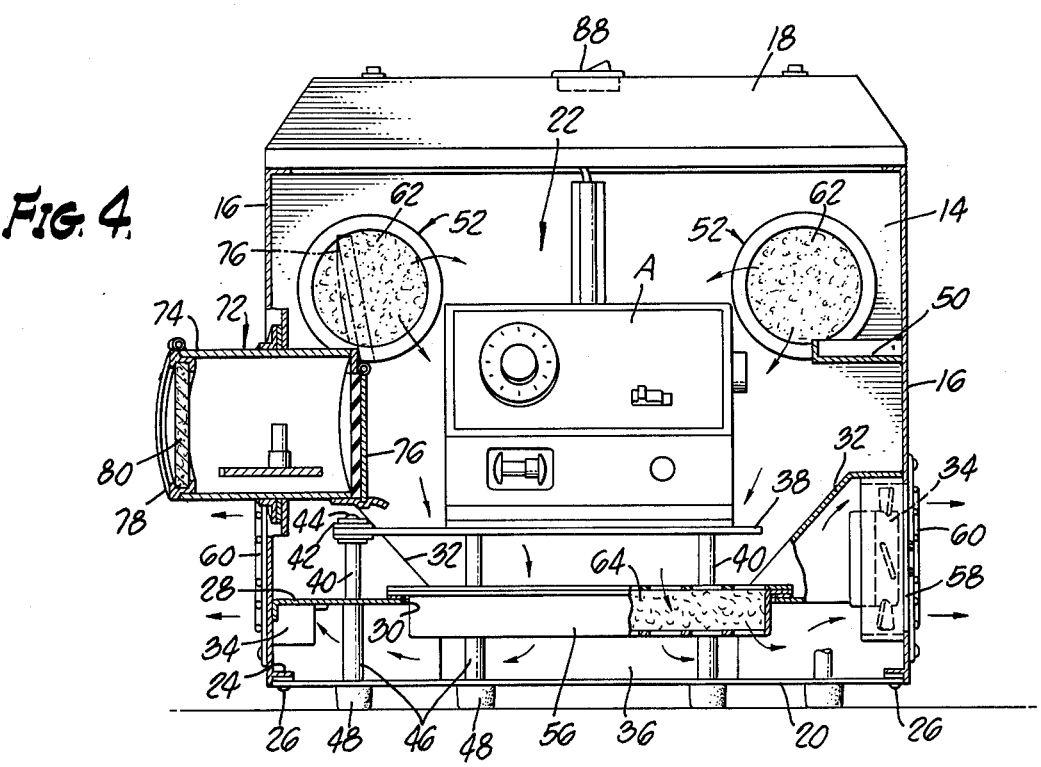

CONTROLLED ENVIRONMENT WORK ENCLOSURE

BACKGROUND OF THE INVENTION

1. Field of the Invention

The present invention relates generally to enclosures for handling hazardous materials and, more particularly, to a controlled atmosphere work enclosure adapted to be used in dental operatories for mixing, mulling, cutting and storing amalgam.

2. Discussion of the Prior Art

Of major national concern are health hazards resulting from environmental pollution. Among the more deadly sources of pollution are the heavy metals, and of these mercury is one of the most hazardous and difficult to control.

Of particular concern are the hazards presented through careless handling of mercury in the dental office and dental laboratory. In fact, the abnormally high rate of suicide among dentists is believed by many experts to be directly linked to Mercury poisoning. Since the dental profession in the United States uses in excess of 200,000 pounds of mercury per year, or about four percent of the total amount used in the United States, a significant threat is presented, not only to the health of the dentist, but to his auxiliary personnel as well.

Environmental contamination through the use of mercury in dental operatories originates primarily from mercury spills and leakage or failure of mercury-containing capsules used in the trituration process. Also contributing to the inordinately high level of mercury contamination found in dental offices and laboratories is carelessness by the dentist and his assistants in mulling, amalgam cutting, and mercury storage. A recent study conducted at the University of Tennessee entitled "Mercury Vapor Experience in a Dental School Environment", JADA 88:785, April 1974, disclosed that seven out of ten dental operatories tested showed mercury vapor levels significantly above the threshold limit of 50 micrograms per cubic meter. This study further revealed that urinary mercury levels tended to parallel vapor exposure and that the urinary level of the average dentist was twice that of the accepted normal level (20.40 micrograms Hg/24 hrs. vs. 9.95 micrograms Hg/24 hrs).

One of the detrimental effects of excessive mercury exposure is acute anxiety. This factor is believed linked with metal illness and it has recently been established through statistical studies that dentists take their own lives twice as often as the general population.

Although mercury contamination poses a particular threat in dental offices and laboratories, the problem is by no means limited to such operatories. Wherever mercury is handled, be it in hospitals, scientific laboratories, or industrial plants, mercury contamination presents a significant health hazard. In hospitals and scientific laboratories, the mercury hazard arises from many sources, including the use of several pieces of apparatus such as the Coulter counter, the Van Slyke apparatus, Miller-Abbot and Cantor tubes.

In recent years, various approaches have been suggested to control mercury contamination in dental operatories, hospitals and laboratories. For example, several types of mercury vapor sensing devices have been developed to monitor mercury vapor levels. Similarly, a wide variety of filtered room exhaust units have been proposed to control atmospheric contamination. Little has been done, however, to prevent the contamination from occurring in the first place. Although expedients such as prepackaged amalgam capsule systems, wherein the mercury and alloy are stored and mixed in cartridges, have come into relatively wide use, such systems have exhibited several disadvantages. In addition to the propensity of the cartridges to leak during storage and to break during mixing operations, their handling and disposal after the amalgam is mixed contributes to environmental contamination.

The principal thrust of the present invention is to attack the mercury contamination problem at its source by providing a safe, compact, reliable, and easy to use controlled environment work station or enclosure wherein all routine mercury handling operations can be accomplished. As will be better understood from the discussion which follows, the work station of the present invention provides a totally enclosed, controlled environment workspace wherein various mercury handling operations such as mixing, mulling, and amalgam cutting, can be accomplished in absolute safety with no fear of personnel or atmospheric contamination. Mercury spills are completely contained within the unit and a novel air lock access arrangement is provided to enable the spilled mercury to be cleaned up without opening the unit to room atmosphere, thereby precluding any possible spread of contamination. All mercury handling operations are conducted through rubber gloves which are sealably connected to the unit so as to prevent personnel contamination through direct handling of the mercury. A unique air circulation system for controlling vaporous and particulate mercury within the system is provided so that a current of air continuously moves downwardly through and around the work platform toward a highly efficient mercury filtering medium. Specially designed filters are also provided at each air inlet port to prevent escape of mercury therethrough in particulate or vapor form.

The work enclosure of the present invention, when used in the dental operatory, is large enough to provide ample space to proportion, load, mix, cut, and store mercury and mercury alloys. Additionally, the work enclosure is designed to accommodate amalgamators of the latest design by providing a specially constructed platform upon which the amalgamator can conveniently be mounted.

Regular use of the work enclosure of the invention by the dentist and his assistants for all amalgam work virtually eliminates the threat of environmental contamination of the operatory with mercury.

When it is desired to use the work station of the invention in hospitals or scientific laboratories, it is to be appreciated that appropriate internal modifications can readily be made to accommodate numerous types of tools and instruments. Additionally, by use of special filters, the enclosure can readily be adapted to safely handle hazardous materials other than mercury such as toxic chemicals, radioactive materials, and the like.

SUMMARY OF THE INVENTION

It is an object of the present invention to provide a compact, self-contained, controlled environment work station in which hazardous materials such as heavy metals, radioactive isotopes, toxic chemicals, and the like, can be safely handled without fear of contamination of the technician, the surrounding atmosphere, or the operational area in which the work enclosure is used.

More particularly, it is an object of the present invention to provide a controlled environment work station adapted for use by the dental profession for mixing, mulling, cutting, and storage of amalgam.

It is another object of the invention to provide a work enclosure of the aforementioned character in which, during use, there is maintained within the enclosure a subatmospheric pressure and in which, due to the location of the air inlet and outlet ports, air is continuously drawn inwardly and then moved rapidly downwardly past a work platform provided intermediate the enclosure.

It is another object of the invention to provide a work enclosure as described in the preceding paragraph in which specially designed filter mediums are operably associated with both the air inlets and the air outlets of the enclosure to preclude the escape of vaporous or particulate materials.

It is still another object of the invention to provide a work enclosure of the class described which is particularly adapted for dental work and can accommodate the dentist's amalgamator and associated amalgam handling equipment.

It is a further object of the invention to provide a work station as described in the previous paragraph in which the work chamber is sufficiently large to conveniently accommodate the amalgamator and to permit the dentist and his assistants to proportion, load, mix, store and dispense amalgam in the normal manner, but without fear of personnel or environmental mercury contamination.

It is still another object of the invention to provide a work enclosure of the class described in which there is included a novel air lock arrangement to permit safe introduction and withdrawal of material from the enclosure during operation without affecting the air flow within the chamber and without risk of contaminating the environment or the surrounding work area.

It is a further object of the invention to provide a work enclosure as described in the preceding paragraphs which is well lighted, includes strategically located viewing panels and in which convenient access to the working area is accomplished through flexible plastic or rubber gloves which are removably affixed to glove rings mounted on the front panel of the unit. The gloves provided are of ample length to reach all areas of the chamber comfortably, are very pliable, and assure complete freedom of movement by the technician.

It is yet another object to provide a work enclosure as previously described which is attractive, sturdy, highly reliable in use, requires minimum maintenance, provides maximum safety to the user, and yet is of a simple design which can be readily and inexpensively manufactured.

These and other objects of the invention are achieved by a controlled environment work enclosure comprising a hollow housing defining a work space; a work platform disposed intermediate the workspace; at least one air inlet provided in the housing above the work platform; an air outlet provided in the housing below the work platform; suction means for maintaining subatmospheric pressure in the work enclosure and for drawing a stream of air in a downward direction through the workspace, past the work platform, toward the air outlet; and filter means interposed in the stream of air for preventing vapors and particulate materials from escaping from the work enclosure through the air outlet.

BRIEF DESCRIPTION OF THE DRAWINGS

FIG. 1 is a perspective view of the controlled environment work enclosure of the present invention.

FIG. 2 is a side elevational cross-sectional view taken along lines 2—2 of FIG. 1.

FIG. 3 is a top view in cross-section of the work enclosure taken along lines 3—3 of FIG. 1.

FIG. 4 is a cross-sectional view taken along lines 4—4 of FIG. 1.

PREFERRED EMBODIMENT OF THE INVENTION

Referring to the drawings, and particularly to FIGS. 1 and 2, the controlled environment work enclosure of the present invention comprises interconnected front, back, side, top and bottom walls 12, 14, 16, 18 and 20 respectively, defining a closed chamber or workspace generally designated by the numeral 22. Bottom wall 20 comprises a flat plate which fits into a gasketed rim 24 provided in the lower margins of the front, back and side walls. Bottom wall 20 is sealably interconnected with the gasketed rim by means of appropriate connectors such as clinch nuts 26. The enclosure walls may be constructed from a wide variety of materials including sheet metal, plastic, fiber composites, and the like, which are suitably interconnected to form a hollow housing by the use of fasteners, bonding materials, or by welding.

A subfloor 28 (FIG. 2) is mounted within the work chamber intermediate the bottom and top walls. Subfloor 28 is provided with a central opening 30 and is sealably connected at its margins with the side, front and back walls as by bonding, spot welding, or the like. The rear corners of the subfloor are formed into two outwardly facing ramps 32 (FIG. 4) to accommodate mounting of tubeaxial fans 34, the purpose of which will presently be described. Preferably, subfloor 28 is sloped or tapered slightly from its corners toward opening 30 to funnel contaminants toward the opening.

As best seen in FIG. 2 and 4, subfloor 28, in cooperation with bottom wall 20, defines an air passageway generally designated by the numeral 36.

Removably mounted within the work chamber intermediate top wall 18 and subfloor 28 is a sturdy, perforated work platform or tray 38. Work platform 38 is supported within the work chamber by vertical supporting columns 40 which extend through subfloor 28 and rest upon bottom wall 20. Tray 38 is resiliently mounted onto vertical columns 40 by means of rubber grommets 42 which are attached to the top of the columns by appropriate fasteners such as screws 44. Platform 38 is configured to support an amalgamator machine, generally designated by the letter "A", of standard design which may be attached to the platform either by clamps, by bonding, or by other suitable fasteners. As indicated in the drawings, platform 38 is sufficiently large to accommodate placement of the amalgamator, as well as various tools and equipment used by the dentist to proportion, load, mix and store amalgam.

Affixed to cylindrical spacers 46, which are telescopically received over columns 40 and extend between bottom wall 20 and subfloor 28, are rubber feet 48 adapted to provide uniform support to the enclosure. Spacers 46 function to provide superior load distribution and minimize warping.

Provided interiorly of the work chamber and affixed to side walls 16 are a plurality of perforated metal shelves 50 (FIGS. 1 and 4) which provide convenient storage space for necessary tools and supplies.

An important feature of the work enclosure of the present invention is the unique air circulation system adapted to provide a continuous downward flow or downdraft of air past the work platform 38. As best seen by referring to FIGS. 2 and 4, air enters the enclosure through a pair of spaced apart air inlet ports 52 provided in back wall 14 above work platform 38. First filter means 54 are replaceably mounted in each of the air inlet ports to prevent passage of contaminants either in vaporous or particulate form through the air inlets. Mounted below the work platform within aperture 30 formed in subfloor 28 is a removable second filter means 56. To create the desired air flow patterns within the work enclosure, there is provided suction means for drawing air into the enclosure through the air inlet ports and urging it rapidly downwardly within the enclosure past work platform 38 and through second filter means 56 into air passageway 36. In the form of the invention shown in the drawings, the suction means comprises the previously identified tubeaxial fan units 34 (FIG. 4) mounted in side walls 16 proximate bottom wall 20. As shown by the directional arrows in FIGS. 2 and 4, fan units 34 function to continuously maintain subatmospheric pressure within the work enclosure and cause a smooth continuous downward flow of air past the work platform and through the apertures formed therein whereby vaporous or particulate material in the vicinity of the work platform will be carried downwardly toward second filter means 56. Filter means 56 will remove the contaminants from the air and with minimal impedance permit the air to flow through air passageway or duct 36 toward the fan units for expulsion to room atmosphere through outlet ports 58 provided in side walls 16. As best seen in FIG. 1, a suitable grille 60 is provided over outlet openings 58 to prevent injury to personnel through contact with the fan blades of the fan unit 34.

When the enclosure of the invention is used in dental operatories for handling amalgam and the like, the first and second filter means of the apparatus comprise replaceable filters of activated charcoal granules. Two small filters 62 comprise the first filter means. These filters are mounted in air inlets 52 and control mercury contaminants resulting from back pressure flow or static pressure migration within the system. A larger filter 64 comprises the second filter means of the invention and is positioned in the central opening 30 provided in subfloor 28. This filter is slightly thicker than the smaller filters 62 and is adapted to catch and absorb mercury vapors as well as liquid mercury resulting in either the amalgamation process or mercury spills which may occur while proportioning the amalgam mixture.

It is to be appreciated that when the enclosure of the invention is used for other purposes, such as handling toxic chemicals or radioactive isotopes, the first and second filter means will comprise replaceable filters designed to effectively filter the particular contaminant being handled.

To enable working access to the interior of the work enclosure, there is provided operator access means shown here in the form of flexible plastic or rubber glove means 66 replaceably affixed to glove rings 68 mounted on the front walls of the enclosure. Glove means 66 seal off the entry ports defined by the glove rings and are of sufficient length to enable the technician to comfortably reach all areas of the work enclosure. The glove means are made of a tough bit pliable material and assure complete freedom of movement by the technician while working in the enclosure. Glove means 66 are replaceably affixed to glove rings 68 by outer rings 70 which slip over the glove rings and hold the glove means captive therebetween.

Air lock means, generally designated by the numeral 72, are provided in a side wall of the enclosure for permitting introduction and withdrawal of articles from the workspace while maintaining subatmospheric pressure within the work enclosure. As best seen by referring to FIG. 4, the air lock means of this form of the invention comprises a generally cylindrically shaped member 74 which extends through and is sealably affixed to side wall 16 by suitable means such as bonding. To provide access to the air lock, member 74 is provided with hingeably connected inner and outer doors 76 and 78. Forming a part of the outer door 78 is filter medium 80 adapted to prevent escape of contaminants through the air lock when the inner door 76 is opened. When the enclosure is used for handling mercury or mercury alloys, filter 80 may be constructed of activated charcoal granules. When the enclosure is used for handling other hazardous materials, filter 80 will be formed of an appropriate material capable of filtering out the particular contaminant being handled. Air lock 72 is of sufficient size to permit passage of a wide variety of tools, equipment and cleaning materials.

Should the interior of the work enclosure become contaminated as a result of a mercury spill, for example, the mercury can be cleaned up from the inside of the unit, placed into plastic bags or other suitable containers, and transferred from the enclosure prior to opening the top of the unit. The air lock means also provides a method of introducing special tools or amalgam during operation of the unit without affecting the controlled environment and without risking spread of contamination.

As illustrated in FIG. 1, the forward portion 18a of the top wall is provided with a viewing panel to enable complete visibility of the amalgamator unit and the work platform 38. This forward portion 18a also forms a pass-through opening or access hatch 19 which is hingeably connected to the rearward portion of the top wall 18 at 82 to permit the panel to be lifted upwardly and swung rearwardly to provide access to the interior of the enclosure. It is to be appreciated that this panel is closed during all operations of the system and is sealably affixed to the side and front walls by means of an appropriate gasket or "O" ring arrangement.

Lighting for the interior of the work enclosure is provided by means of a fluorescent fixture 84 mounted on the rearward portion of top wall 18. Provided at the rearward portion of subfloor 28 is an electrical outlet 86 adapted to supply power interiorly of the enclosure to operate the amalgamator unit or other electrically powered equipment which may be used within the enclosure. A single electrical rocker type swich 88 is mounted in top wall 18. Switch 88 is suitably connected with an external source of electric power and controls the current flow to the chamber. Operation of switch 88 turns on fluorescent light 84, starts blower fans 34, and energizes electrical outlet 86.

Operation

With the necessary tools, equipment, supplies and amalgam placed within the unit, the top hatch 19 is closed and sealed against the gasket member. Operation of switch 88 then energizes the light and causes the blower fans 34 to begin to rotate. Rotation of the fans causes air to be drawn into the enclosure through inlet ports 52. Because of the size and location of the inlet ports relative to the outlet ports, air will be drawn rapidly downwardly as indicated by the directional arrows, past and through the work platform, toward filter 64. Any mercury vapors or liquid mercury in the vicinity of the work platform will therefore be urged downwardly away from the operator and into the filter where the mercury will be removed from the air stream. The air will then be drawn through the filter into air passageway 36 and urged outwardly through outlet ports 58.

With the air circulating in the manner described, the operator may safely mix, mull and cut the amalgam in the normal fashion with no fear of contaminating himself or the environment. After the work is completed, and assuming there has been no failure of the amalgam capsules or spillage of mercury, the operator can wipe the work platform and amalgamator unit with cleaning swipes and a suitable solvent, place the swipes into a plastic bag, and seal it. With the fans still operating, the enclosure may then be opened by lifting the access hatch and the mixed amalgam can be removed for use by the dentist.

Should there be an accident during the mixing operations resulting in spillage of mercury, the downdraft flow of air within the chamber can be allowed to continue while necessary cleaning solvents and swipes are introduced through the air lock. The spilled mercury can then be completely cleaned up, placed into plastic bags or containers which can be sealed, and then, and only then may the forward hatch be opened to permit removal of the amalgam.

After a predetermined period of operation, perhaps on the order of 30 days, the contaminated filter 64 can be removed from the outlet port of the enclosure, placed in a sealed container, and removed through the access hatch 19. After a new filter is installed, the contaminated filter can be returned in its sealed container to the enclosure for mercury reclamation. Although the smaller inlet filters 62 do not require replacement as frequently as filter 64, when replacement is necessary, such replacement and mercury reclamation can be accomplished in the manner previously described.

With regard to the actual mixing and manipulation of the amalgam within the enclosure, it is to be appreciated that this can be done in basically the same manner as the work is now being done in dental offices and laboratories. For example, with the amalgam in place in the enclosure, the technician can slip his hands into the glove means and proceed to proportion, measure, and fill the mixing capsules with the alloy pill and mercury. The filled capsule is then positioned within the amalgamator and the amalgamator energized in the normal fashion. After mixing is accomplished, the technician opens the capsule, places the amalgam into an appropriate receptacle which may be set on the top shelf 50 near the hatch. The technician then removes his hands from the gloves and waits for a few moments to make certain that the air circulation system is properly functioning. With the blower fans continuing to run, the technician can then open the access hatch and remove the amalgam. The hatch is then closed and switch 88 closed to de-energize the work enclosure.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and the spirit of the invention, as set forth in the following claims.

We claim:
1. A controlled subatmospheric pressure environment work enclosure comprising:
   a. a hollow housing defining a work space;
   b. a work platform disposed intermediate said work space;
   c. at least one air inlet provided in said housing above said work platform for permitting air to be drawn inwardly from the exterior of said housing;
   d. an air outlet provided in said housing below said work platform adapted to permit air to be ejected from said housing;
   e. suction means for maintaining subatmospheric pressure in said work enclosure and for continuously drawing a stream of air inwardly through said air inlet and then rapidly in a downward direction through said work space past said work platform toward said air outlet for ejection therethrough; and
   f. filter means interposed in said stream of air for filtering the air flowing past said work platform thereby preventing vapors and particulate materials contained therein from escaping from said work enclosure to the exterior of said housing through said air outlet.

2. A controlled environment work enclosure as defined in claim 1 in which two spaced apart air inlets are provided in said housing above said work platform, said inlets being arranged to cooperate with said suction means to cause a smooth, continuous and downward flow of air past said work platform whereby vapors or particulate material in the vicinity of said work platform will be carried downwardly toward said air outlet.

3. A controlled environment work enclosure as defined in claim 2 including:
   a. operator access means provided in said housing to enable manipulation of articles located therewithin while maintaining subatmospheric pressure within said work enclosure;
   b. air lock means provided in said housing for permitting introduction and withdrawal of articles from said work space while maintaining subatmospheric pressure in said work enclosure; and
   c. inlet filter means cooperatively associated with said air inlets for preventing escape of vapor and particulate material therethrough.

4. A controlled environment work enclosure as defined in claim 3 in which said filter means and said inlet filter means comprise replaceable filter units having a filtering medium consisting of a multiplicity of activated charcoal granules.

5. A controlled subatmospheric pressure environment work enclosure for use in mixing, mulling, cutting, and storing amalgam comprising:
   a. interconnected front, back, side, bottom, and top walls defining an enclosed work space, said top wall having a viewing panel provided therein;

b. a perforated work platform disposed intermediate said top and bottom walls;

c. glove means replaceably mounted on said front wall for receiving the hands of an operator and permitting manipulation of articles disposed upon said work platform;

d. at least one air inlet provided in said back wall above said work platform for permitting air to be drawn inwardly from the exterior of said working enclosure;

e. first filter means cooperatively associated with said air inlet for preventing passage therethrough to the exterior of said enclosure of mercury in vapor or particulate form;

f. an air outlet provided in said bottom wall below said work platform for permitting the ejection of air from said enclosure;

g. suction means for continuously maintaining subatmospheric pressure in said work station and for continuously drawing a stream of air inwardly through said air inlet and then rapidly in a downward direction from said air inlet past said work platform in a direction toward said air outlet; and h. second filter means interposed in said stream of air for filtering the air passing past said work platform thereby preventing mercury in vapor or particulate form contained therein from escaping from said work station through said air outlet.

6. A controlled environment work enclosure as defined in claim 5 including two spaced apart air inlets so positioned as to cooperate with said suction means to create a continuous downdraft of air around said work platform and through the perforations therein whereby vapors or particulate materials on said platform will be urged downwardly toward said filter means.

7. A controlled environment work enclosure as defined in claim 6 in which said suction means comprises a pair of fan units mounted in said side walls proximate said bottom wall for drawing air from said air inlets downwardly through said work space.

8. A controlled environment work enclosure as defined in claim 7 including a subfloor mounted within said work space intermediate said bottom wall and said work platform, said subfloor being adapted to carry said second filter means and being connected with said side walls to define a duct in open communication with said fan units whereby air will be drawn inwardly through said air inlets, downwardly through said filter means, and into said duct.

9. A controlled subatmospheric pressure environment work enclosure for use in combination with an amalgamation unit for mixing, mulling, cutting, and storing amalgam comprising:

a. interconnected front, back, side, top and bottom walls defining a closed chamber, said top wall having a pass-through opening therein;

b. a subfloor mounted within said chamber intermediate said bottom and top walls, said subfloor having a central opening therein and being sealably connected at its margins with said side, front and back walls to define, in cooperation with said bottom wall, an air passageway;

c. a perforated work platform disposed intermediate said top wall and said subfloor, said work platform being adapted to support the amalgamation unit;

d. a pair of spaced apart air inlet ports provided in said back wall above said work platform for permitting air to be drawn inwardly from the exterior of said work enclosure;

e. first filter means replaceably mounted in said air inlet ports for preventing passage of mercury therethrough to the exterior of said enclosure;

f. second mercury filter means replaceably mounted in said central opening in said subfloor; and g. suction means mounted below said subfloor for drawing air into said enclosure from the exterior of said work enclosure, through said air inlet ports and urging it downwardly within the closure past said work platform and through said second filter means into said air passageway for ejection to the exterior to said work enclosure.

10. A controlled environment work enclosure as defined in claim 9 in which said suction means comprises a pair of fan units mounted in said side walls below said subfloor in connection with said air passageway and adapted to maintain subatmospheric pressure within said air passageway.

* * * * *